(12) United States Patent
Gottlieb et al.

(10) Patent No.: US 8,589,086 B2
(45) Date of Patent: Nov. 19, 2013

(54) METHOD AND SYSTEM FOR SPECTROSCOPIC DATA ANALYSIS

(75) Inventors: Paul Gottlieb, Taringa (AU); Michael Barnes, Karana Downs (AU); Brian William Bourke, Malvern (AU)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/153,914

(22) Filed: Jun. 6, 2011

(65) Prior Publication Data
US 2011/0301869 A1 Dec. 8, 2011

Related U.S. Application Data

(63) Continuation of application No. 12/368,176, filed on Feb. 9, 2009, now Pat. No. 7,979,217, which is a continuation of application No. 10/911,057, filed on Aug. 3, 2004, now Pat. No. 7,490,009.

(51) Int. Cl.
G01N 31/00 (2006.01)

(52) U.S. Cl.
USPC .............................. 702/32; 378/83

(58) Field of Classification Search
USPC ........... 356/300, 326; 702/30, 32; 378/44–50, 378/82–85
See application file for complete search history.

(56) References Cited

U.S. PATENT DOCUMENTS

| 4,037,101 A | 7/1977 | Okumura et al. |
| 4,476,386 A | 10/1984 | Reid et al. |
| 4,592,082 A | 5/1986 | Pawloski |
| 4,839,516 A | 6/1989 | Freeman et al. |
| 5,555,198 A | 9/1996 | Asano |
| 5,741,707 A | 4/1998 | Herron et al. |
| 5,798,525 A | 8/1998 | Benizri-Carl et al. |
| 5,866,903 A | 2/1999 | Morita et al. |
| 5,906,919 A | 5/1999 | Garini et al. |
| 5,991,028 A | 11/1999 | Cabib et al. |
| 6,018,587 A | 1/2000 | Cabib |
| 6,066,459 A | 5/2000 | Garini et al. |
| 6,122,343 A | 9/2000 | Pidcock |
| 6,282,301 B1 | 8/2001 | Haskett |

(Continued)

FOREIGN PATENT DOCUMENTS

| CN | 1601261 | 3/2005 |
| JP | 08015185 | 1/1996 |

(Continued)

OTHER PUBLICATIONS

Ashton, Edward A. et al., "Multialgorithm Solution for Automated Multispectral Target Detection," Opt. Eng., Apr. 1999, pp. 717-724, vol. 38, No. 4.

(Continued)

*Primary Examiner* — Kara E Geisel
(74) *Attorney, Agent, or Firm* — Scheinberg & Associates, PC; Michael O. Scheinberg

(57) ABSTRACT

A method of analyzing spectroscopic data, the method comprising collecting spatially resolved measurement spectroscopic data of a sample for a series of measurements spots, assigning the measurement spots into a predefined set of spectral categories, based on characteristics of the spectroscopic data of the respective measurement spots, identifying groupings of the measurement spots based on their respective spectral categories and their spatial relationships, and assigning each grouping of measurement spots to a fundamental sample unit data object.

18 Claims, 7 Drawing Sheets

(56) References Cited

U.S. PATENT DOCUMENTS

| | | |
|---|---|---|
| 6,341,257 B1 | 1/2002 | Haaland |
| 6,377,652 B1 | 4/2002 | Sturm |
| 6,466,929 B1 | 10/2002 | Brown et al. |
| 6,470,335 B1 | 10/2002 | Marusak |
| 6,584,413 B1 | 6/2003 | Keenan et al. |
| 6,658,143 B2 | 12/2003 | Hansen et al. |
| 6,674,894 B1 | 1/2004 | Parker et al. |
| 6,687,620 B1 | 2/2004 | Haaland et al. |
| 6,711,503 B2 | 3/2004 | Haaland |
| 6,724,940 B1 | 4/2004 | Qian et al. |
| 6,842,702 B2 | 1/2005 | Haaland et al. |
| 6,993,170 B2 | 1/2006 | Johnson et al. |
| 7,139,415 B2 | 11/2006 | Finkbeiner |
| 7,161,672 B2 | 1/2007 | Gornushkin et al. |
| 7,400,770 B2 | 7/2008 | Keaton et al. |
| 7,436,510 B2 | 10/2008 | Grun et al. |
| 7,490,009 B2 | 2/2009 | Gottlieb et al. |
| 7,979,217 B2 | 7/2011 | Gottlieb et al. |
| 2002/0169589 A1 | 11/2002 | Banki et al. |
| 2004/0027350 A1 | 2/2004 | Kincaid et al. |
| 2004/0147830 A1 | 7/2004 | Parker et al. |
| 2005/0037515 A1 | 2/2005 | Nicholson et al. |
| 2005/0165290 A1* | 7/2005 | Kotsianti et al. .............. 600/407 |
| 2006/0291619 A1 | 12/2006 | Statham |
| 2007/0279629 A1 | 12/2007 | Grun et al. |

FOREIGN PATENT DOCUMENTS

| | | |
|---|---|---|
| JP | 2000249668 | 9/2000 |
| JP | 2001066269 | 3/2001 |
| JP | 2002-189005 | 7/2002 |
| JP | 2002189005 | 7/2002 |
| RU | 2054660 | 2/1996 |
| WO | 9905503 | 2/1999 |
| WO | 2009100404 | 8/2009 |

OTHER PUBLICATIONS

Benz, Ursula C. et al., "Multi-resolution, Object-oriented Fuzzy Analysis of Remote Sensing Data for GIS-ready Information," ISPRS Journal of Photogrammetry & Remote Sensing, 2004, pp. 239-258, vol. 58.

Creelman, Robert A. et al., "A Scanning Electron Microscope Method for Automated, Quantitative Analysis of Mineral Matter in Coal," International Journal of Coal Geology, 1996, pp. 249-269, vol. 30.

Ghassemian, Hassan et al., "Object-Oriented Feature Extraction Method for Image Data Compaction," IEEE Control Systems Magazine, Jun. 1998, pp. 42-48.

Gottlieb, P. et al., "The Automatic Identification and Quantification of Silver Minerals," XVIII International Mineral Processing Congress, May 23-28, 1993, pp. 475-481, Sydney, Australia.

Gottlieb, P. et al., "Using Quantitative Electron Microscopy for Process Mineralogy Applications," Microtextural Mineralogy, Apr. 2000, pp. 24-25.

Hazel, Geoffrey G. et al., "Object-level Processing of Spectral Imagery for Detection of Targets and Changes Using Spatial-Spectral Temporal Techniques," Proceeding of the SPIE, 2001, pp. 380-390, vol. 4381.

Newbury, Dale E., "Chemical Compositional Mapping by Microbeam Analysis at the Micrometer Scale and Finer," Microelectronics Journal, 1997. pp. 489-508, vol. 28.

Sutherland, D.N. et al., "Application of Automated Quantitative Mineralogy in Mineral Processing," Minerals Engineering, 1991, pp. 753-762, vol. 4, Nos. 7-11.

Sutherland, David N., "Image Analysis for Off-Line Characterisation of Mineral Particles and Prediction of Processing Properties," Part. Part. Syst. Charact., 1993, pp. 271-274, vol. 10.

Gottlieb, Paul, et al., "Using Quantitative Electron Microscope for Process Mineralogy Applications," Microtextural Mineralogy, Testing & Analysis, Apr. 2000, pp. 24-25, vol. 52, No. 4.

Gu, Ying, "Automated Scanning Electron Microscope Based Mineral Liberation Analysis," Journal of Minerals & Materials Characterization & Engineering, 2003, p. 33-41, vol. 2, No. 1.

Newbury, Dale E., "Chemical compositional mapping by microbeam analysis at the micrometer scale and finer," Microelectronics, 1997, pp. 489-508, vol. 28.

"Forensic Geoscience: Principles, Techniques and Applications," The Geology Society International Conference, Mar. 3 & 4, 2003, 55 pgs.

Pye, Kenneth, et al., "Forensic Geoscience: Principles, Techniques and Applications," The Geology Society International Conference, Mar. 3 & 4, 2003, 26 pgs, No. 232.

* cited by examiner

METHOD AND SYSTEM FOR SPECTROSCOPIC DATA ANALYSIS

This application is a Continuation application of U.S. application Ser. No. 12/368,176, filed Feb. 9, 2009, which is a Continuation application of U.S. application Ser. No. 10/911,057, filed on Aug. 3, 2004, which is U.S. Pat. No. 7,490,009, which are hereby incorporated by reference.

FIELD OF INVENTION

The present invention relates broadly to a method and system for analyzing spectroscopic data, and to a computer readable medium having stored thereon program code means for instructing a computer to execute a method of analyzing spectroscopic data.

BACKGROUND

Spectroscopic tools such as electron beam induced X-ray signal or back scattered electron signal spectroscopy using a scanned electron beam can provide data from a material sample. From that data, mineral, compositional, elemental or phase maps can be formed, or from which at specified image points the phase, mineral composition, or elemental composition present at those points can be identified.

Such tools were initially mainly used for what may be referred to as fundamental research at Universities and research laboratories. The technology surrounding such tools has matured to a point where they are now more commonly found in commercial operations, such as their use by mining companies to facilitate assessment and exploration at a particular plant or prospecting area.

As a result of this shift in the application environment for such spectroscopic tools, a major challenge now is to provide the analytical tools complementing the spectroscopic tools. The analytical tools should enable powerful and flexible processing and statistical analysis of the spectroscopic data obtained.

It is with the knowledge of the above-mentioned challenge and problems with existing solutions that the present invention has been made, and is now reduced to practice.

SUMMARY

In accordance with a first aspect of the present invention there is provided a method of analyzing spectroscopic data, the method comprising:

collecting spatially resolved measurement spectroscopic data of a sample for a series of measurements spots, assigning the measurement spots into a predefined set of spectral categories, based on characteristics of the spectroscopic data of the respective measurement spots, identifying groupings of the measurement spots based on their respective spectral categories and their spatial relationships, and assigning each grouping of measurement spots to a fundamental sample unit data object.

The method may further comprise assigning one or more properties to each spectral category.

The method may further comprise assigning general information, including measurement information and/or sample information, to each fundamental sample unit data object.

The method may further comprise calculating one or more derived properties for each fundamental sample unit data object based on one or more of a group comprising the measurement spots assigned to the fundamental sample unit data object, the properties assigned to the spectral categories of the measurement spots, the general information assigned to the fundamental sample unit data object, and the spatial relationships of the measurement spots.

The derived properties may comprise one or more of a group comprising mass, area, perimeter, volume, size and density.

The predefined set of spectral categories may comprise a hierarchical grouping of categories.

The method may further comprise utilizing a hierarchical structure of general information data objects that embody the hierarchical relationships of the general information assigned to the fundamental sample unit data objects, with relationships defined as being either "up" the hierarchy, that is away from the fundamental sample unit data objects, or "down" the hierarchy, that is towards the fundamental sample unit data object, and wherein the general information assigned to a fundamental sample unit data object is stored in the general information data object in the hierarchical structure that represents the manner in which the general information data is shared by the fundamental sample unit data objects.

Data items obtainable from each general information data object in the hierarchical structure may comprise all of the data items stored in the general information data object, plus all data items obtainable from general information data objects further "up" the hierarchical structure.

The hierarchical structure and choice of storage locations within the hierarchical structure may follow a predefined pattern.

The hierarchical structure and choice of storage locations within the hierarchical structure may be determined and changed dynamically as-needed.

The method may further comprise formulating an analysis query, defining the analysis query as a sequential series of processing stages, each processing stage having one or more inputs and one or more outputs, and wherein, during execution of the analysis query, one or more of the fundamental sample unit data objects are sequentially provided to each processing stage input as input streams, and processed and output as respective output streams of fundamental sample unit data objects at each processing stage output, and wherein the output stream or streams from one processing stage are the input streams for the next processing stage in the sequential series of processing stages.

The processing at each processing stage may comprise one or more logical expressions for assigning each fundamental sample unit data object to one of the outputs of the processing stage, and/or a process by which a new fundamental sample unit data object is created, differing from the original fundamental sample unit data object, but inheriting its general information and retaining a reference back to the original fundamental sample unit data object.

The new fundamental sample unit data object may be created to separate respective groupings of measurement spots which were initially assigned to one fundamental sample unit data object.

One of the processing stages may produce a statistically representative population of fundamental sample unit data objects as the output stream for normalization processing in subsequent processing stages.

The statistically representative population of fundamental sample unit data objects may comprise fundamental sample unit data objects from different samples.

In accordance with a second aspect of the present invention there is provided a system of analyzing spectroscopic data, the system comprising a data collection unit for collecting spatially resolved measurement spectroscopic data of a sample for a series of measurements spots, and a processor unit assigning the measurement spots into a predefined set of spectral categories, based on characteristics of the spectroscopic data of the respective measurement spots, identifying groupings of the measurement spots based on their respective spectral categories and their spatial relationships, and assigning each grouping of measurement spots to a fundamental sample unit data object.

The processor unit may further assign one or more properties to each spectral category.

The processor unit may further assign general information, including measurement information and/or sample information, to each fundamental sample unit data object.

The processor unit may further calculate one or more derived properties for each fundamental sample unit data object based on one or more of a group comprising the measurement spots assigned to the fundamental sample unit data object, the properties assigned to the spectral categories of the measurement spots, the general information assigned to the fundamental sample unit data object, and the spatial relationships of the measurement spots.

The derived properties may comprise one or more of a group comprising mass, area, perimeter, volume, size and density.

The predefined set of spectral categories may comprise a hierarchical grouping of categories.

The system may further comprise a memory unit for storing a hierarchical structure of general information data objects that embody the hierarchical relationships of the general information assigned to the fundamental sample unit data objects, with relationships defined as being either "up" the hierarchy, that is away from the fundamental sample unit data objects, or "down" the hierarchy, that is towards the fundamental sample unit data object, and wherein the general information assigned to a fundamental sample unit data object is stored in the general information data object in the hierarchical structure that represents the manner in which the general information data is shared by the fundamental sample unit data objects.

Data items obtainable from each general information data object in the hierarchical structure may comprise all of the data items stored in the general information data object, plus all data items obtainable from general information data objects further "up" the hierarchical structure.

The hierarchical structure and choice of storage locations within the hierarchical structure may follow a predefined pattern.

The hierarchical structure and choice of storage locations within the hierarchical structure may be determined and changed dynamically as-needed.

The system may further comprise an interface unit for formulating an analysis query, and an analysis unit defining the analysis query as a sequential series of processing stages, each processing stage having one or more inputs and one or more outputs, and wherein, during execution of the analysis query, one or more of the fundamental sample unit data objects are sequentially provided to each processing stage input as input streams, and processed and output as respective output streams of fundamental sample unit data objects at each processing stage output, and wherein the output stream or streams from one processing stage are the input streams for the next processing stage in the sequential series of processing stages.

The processing at each processing stage may comprise one or more logical expressions for assigning each fundamental sample unit data object to one of the outputs of the processing stage, and/or a process by which a new fundamental sample unit data object is created, differing from the original fundamental sample unit data object, but inheriting its general information and retaining a reference back to the original fundamental sample unit data object.

The new fundamental sample unit data object may be created to separate respective groupings of measurement spots which were initially assigned to one fundamental sample unit data object.

One of the processing stages may produce a statistically representative population of fundamental sample unit data objects as the output stream for normalization processing in subsequent processing stages.

The statistically representative population of fundamental sample unit data objects may comprise fundamental sample unit data objects from different samples.

In accordance with a third aspect of the present invention there is provided a computer readable data storage medium having stored thereon program code means for instructing a computer to execute a method of analyzing spectroscopic data, the method comprising collecting spatially resolved measurement spectroscopic data of a sample for a series of measurements spots, assigning the measurement spots into a predefined set of spectral categories, based on characteristics of the spectroscopic data of the respective measurement spots, identifying groupings of the measurement spots based on their respective spectral categories and their spatial relationships, and assigning each grouping of measurement spots to a fundamental sample unit data object.

In accordance with a fourth aspect of the present invention there is provided a method of analyzing spectroscopic data, the method comprising collecting spatially resolved measurement spectroscopic data of a sample for a series of measurements spots, assigning the measurement spots into a predefined set of spectral categories, based on characteristics of the spectroscopic data of the respective measurement spots, identifying groupings of the measurement spots based on their respective spectral categories and their spatial relationships, assigning each grouping of measurement spots to a fundamental sample unit data object;

assigning general information, including measurement information and/or sample information, to each fundamental sample unit data object;

wherein, during sequential processing of the fundamental sample unit data objects in a processing stage, one or more new fundamental sample unit data objects based on an original fundamental sample unit data object are created, wherein the new fundamental sample unit data objects inherit the general information assigned to the original fundamental sample unit data object and retain a reference back to the original fundamental sample unit data object, and each new fundamental sample unit data object is passed to one or more processing stage outputs.

In accordance with a fifth aspect of the present invention there is provided a system analyzing spectroscopic data, the system comprising a data collection unit for collecting spatially resolved measurement spectroscopic data of a sample for a series of measurements spots, and a processor unit assigning the measurement spots into a predefined set of spectral categories, based on characteristics of the spectroscopic data of the respective measurement spots, identifying groupings of the measurement spots based on their respective spectral categories and their spatial relationships, assigning each grouping of measurement spots to a fundamental sample unit data object, assigning general information, including measurement information and/or sample information, to each fundamental sample unit data object;

wherein, during sequential processing of the fundamental sample unit data objects in a processing stage, the processor unit creates one or more new fundamental sample unit data objects based on an original fundamental sample unit data object, wherein the new fundamental sample unit data objects inherit the general information assigned to the original fundamental sample unit data object and retain a reference back to the original fundamental sample unit data object, and passes each new fundamental sample unit data object to one or more processing stage outputs.

In accordance with a sixth aspect of the present invention there is provided a computer readable data storage medium having stored thereon program code means for instructing a computer to execute a method of analyzing spectroscopic data, the method comprising collecting spatially resolved measurement spectroscopic data of a sample for a series of measurements spots, assigning the measurement spots into a predefined set of spectral categories, based on characteristics of the spectroscopic data of the respective measurement spots, identifying groupings of the measurement spots based on their respective spectral categories and their spatial relationships, assigning each grouping of measurement spots to a fundamental sample unit data object;

assigning general information, including measurement information and/or sample information, to each fundamental sample unit data object;

wherein, during sequential processing of the fundamental sample unit data objects in a processing stage, one or more new fundamental sample unit data objects based on an original fundamental sample unit data object are created, wherein the new fundamental sample unit data objects inherit the general information assigned to the original fundamental sample unit data object and retain a reference back to the original fundamental sample unit data object, and each new fundamental sample unit data object is passed to one or more processing stage outputs.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
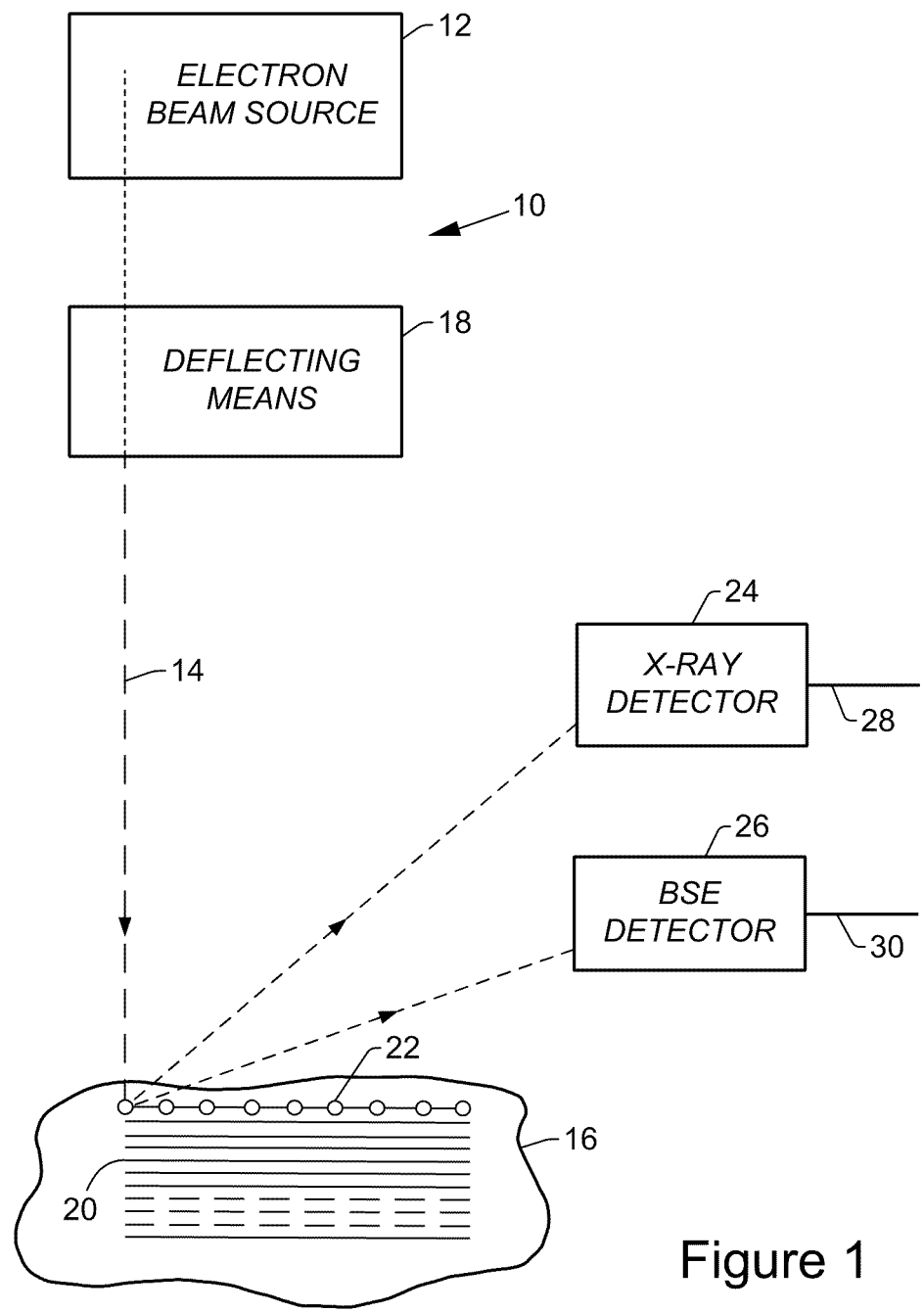
FIG. 1 is a schematic drawing illustrating a spectroscopic tool for conducting sample measurements.

FIG. 1 is a schematic drawing illustrating the components of a spectroscopic system for quantitative evaluation of materials by scanning electron microscopy. The system comprises a Scanning Electron Microscope (SEM) component 10 consisting of an electron beam source 12 producing a collimated beam 14 of electrons, which is directed onto a sample 16 to be analyzed. The SEM 10 further comprises a deflecting means 18 to cause the beam 14 to scan the surface of the sample 16 in a spatially resolved manner, for example a suitable raster pattern such as the series of parallel lines 20 shown in FIG. 1.

The sample is typically part of a sample block and each sample block may be part of a series of sample blocks. The SEM may include a mechanical stage system for selecting a series of "fields of view" on a given sample block and/or a series of sample blocks for measurement.

In operation, the beam 14 is moved along each line in succession and is caused to pause at successive ones of a series of spots e.g. 22 in each line. X-ray photons and back scattered electrons produced at each of the spots e.g. 22 pass to two detectors 24, 26 respectively, for collecting of X-ray signal spectroscopic data and BSE signal spectroscopic data associated with the respective spots e.g. 22. The X-ray detector 24 in the example embodiment is an energy dispersive detector and produces, for each spot e.g. 22, a time spaced series or spectrum of X-ray signals of amplitudes which are representative of energies of X-rays generated at that spot e.g. 22 pursuant to the incidence of the beam 14 thereon.

BSE detector 26 in the example embodiment similarly produces an analogue signal representative of the intensity of back scattered electrons at the spot e.g. 22 upon which the beam 14 is incident.

For a detailed description of a possible operation scheme or technique for systems for quantitative evaluation of materials with systems such as the one described above with reference to FIG. 1, reference is made to U.S. Pat. No. 4,476,386, the contents of which are hereby incorporated by cross reference.

Based on these general principles relating to the obtaining of spectroscopic data from a physical sample, an example embodiment of the present invention will now be described.

Figure 2:
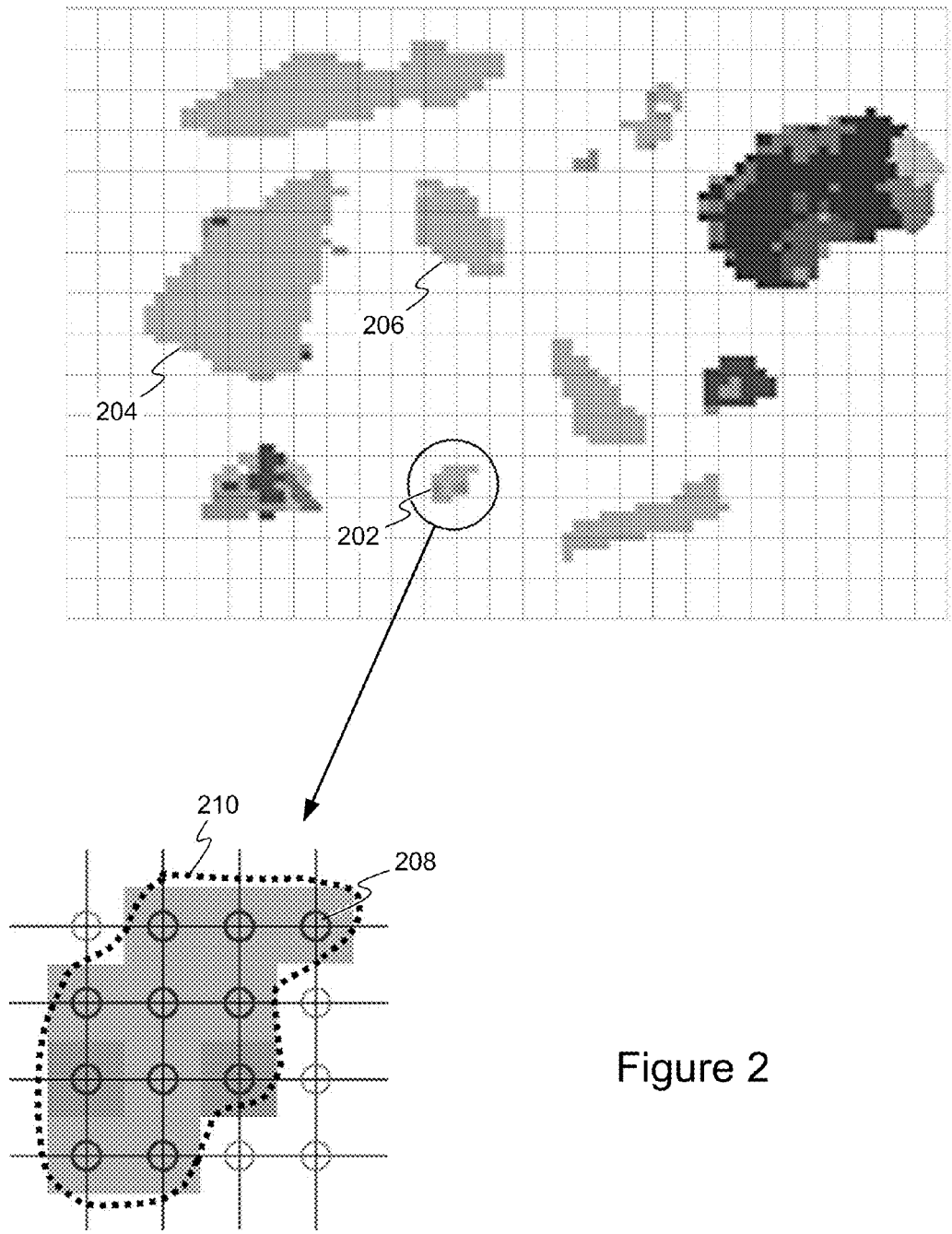
FIG. 2 is a schematic drawing illustrating the relationship between measurement spots and fundamental sample units according to an embodiment of the present invention.

Depending on, inter alia, the size of the probe beam, the raster parameters, and the actual sample, spectral data measurements are made and grouped into clusters that correspond to the physical particles in the sample e.g. 202, 204, 206 as illustrated in FIG. 2. Each measured spot e.g. 208 is assigned a spectral category, by comparing the measured spectral data from that spot to a predefined set of spectral categories. A particle entity is created for each cluster e.g. 210 of measured spots e.g. 208 identified as belonging to one physical particle e.g. 202 in the example embodiment.

Each particle entity e.g. 202, 204, 206 is uniquely identified within the data structure of the example embodiment. The data representation of each particle entity 202, 204, 206 functions as a fundamental sample unit. All further data entities in the data structure of the example embodiment exist for the purposes of organizing, processing or analyzing the fundamental sample unit entities.

The particle entities retain their unique identity throughout the analysis, which means that, at any time, the identity and unique properties of any particle entity can be determined. By dealing with particle entities as the fundamental unit in the example embodiment, and retaining the unique identities, it is possible to perform a variety of ad-hoc statistical analyses on a population of measured particle entities. It also makes it possible to easily identify and extract sub-populations from the particle entities.

As a key feature of the example embodiment, while basic categories (for example physical properties such as density or chemical composition) are assigned at the measurement spot level, according to spectral category, derived properties are calculated at the fundamental sample unit level. General information about the source of the sample is also assigned at the fundamental sample unit level.

In the example embodiment, the data is organized into a hierarchical structure of inter related data objects. For the example embodiment a generic data organization has been developed that allows representation of the interrelationships between different samples, and allows subdivision of the sample for analysis purposes. A "sample" in the example embodiment is a physical sampling of material, for example material taken from a processing plant, site or drill hole, or other source for which analysis is required. The data organization is designed to store all of the essential information required for analysis, and to avoid duplication of data, minimizing storage and avoiding replication issues.

General information relevant to e.g. the structure and measurement is separable from the measurement data itself. The general information may include details such as: where the original sample came from, how it was sampled, how the sample was prepared and how the samples relate to each other. Some of the advantages provided by these separations within the data organization are:

The general information can be changed without affecting the measurement data.

The methods relevant to the data analysis and reporting can be maintained and updated without affecting the general information or the measurement data.

One of the issues is the mechanism by which one defines data structure and interrelationships. For example, each specific field of application will have unique requirements for data organization and storage of the data fields. These requirements will depend on how the sample is sourced and the sample material itself.

In the example embodiment the data organization allows the use of "plug-in data schemas" to establish the data organization. The separation of the general information from the measurement data facilitates the use of such plug-in schemas. This separation relies on encapsulating and "black boxing" the details of the data organization, so that the details are hidden from other parts of the analysis system. The "black box" data organization is implemented as an independent module. In the example embodiment such modules are referred to as a "schema". To the rest of the analysis system, all schemas present a uniform external interface. Internally their structure can be implemented in any manner, so long as the external interface can conform to the standard.

In the example embodiment the hierarchical nature of the data organization is called the Sample Schema. Sample Schemas are available for a variety of application types. Sample schemas vary depending on the type of material being measured and the type of analysis required. For example, a sample schema for forensic type analysis of data may have different relationship terms in the hierarchy and/or a different number of levels. Schemas could equally be implemented for geological, petrochemical or any other application of the technology. The present embodiment shows an implementation of a schema specialized for metallurgical analysis. The analysis methods can be configured to include any or all of these schemas, without need for alterations to the methods outside of the schema.

The data analysis methods are set up to allow plug and play of as many different sample schemas as required, for example: plant processing, mining exploration, coal, flyash, along with the metallurgical, forensics, etc. mentioned above. The processing relies on the existence of a data structure, not on any particular type of sample schema. This is driven by the need to have an analysis tool across the full range of use of technology applications. The ability to separate the measurement data (or particles) from the Sample Schema data allows for data analysis and re-analysis by any predetermined or customized Sample Schema.

In the example embodiment, the plug-in schema is for metallurgical type samples. This will now be described. At the top of the hierarchical structure of inter-related data objects are the "Company" objects, each representing a business entity. Each company object contains one or more "Operation" objects representing sites, plants or divisions within the company. Each operation in turn can contain "Survey" objects representing a particular chronological point when a set of samples were taken. Each survey then contains "Sample" objects, which correspond to the physical samples of material taken during the survey. Each sample then contains a number of "Fraction" objects, corresponding to physical subdivision of the sample material based on its particle size, which occurs during preparation for measurement. Each fraction contains "Sample Block" objects, corresponding to a physical block of material prepared for placement in the SEM. Each sample block then has "Measurement" objects corresponding to an actual measurement of that block in a SEM. Each measurement object contains "Particle" objects that correspond to the particle entities, i.e. clusters of measurement spots that were identified as constituting a single distinct particle on the sample block in the example embodiment. Amongst other things, each particle object contains the data for the spectral category of each measurement spot it includes.

In the example embodiment, the hierarchy is expressed as a structure of data objects stored in an object-oriented database referred to as a "Datastore". The datastore also contains data objects for the sets of spectral category information and objects that embody the particle processing stream.

As the person skilled in the art will appreciate, there are countless varieties of spectral categories. These categories are based on the various spectral patterns arising from the nature of the physical composition of the material such as element or compound or combination thereof and may even include more subtle attributes of the sample material such as textural properties. The sample material would typically contain unknown blends of material. Furthermore it is expected the volume of sample material excited by the electron beam in any single spot may contain a plurality of materials. The outcome is an extensive range of available spectral categories which in most cases is far too detailed to use as the basis for analyses.

A "species identification profile" or SIP can be used to group the measured X-Ray spectra into a first level of the predetermined spectral categories. In the example embodiment, the SIP is an extensive library which maps measurement spectra patterns to spectral categories. For ease of interpretation and data analysis, the SIP may still provide too much detail, and it may be more desirable to consider the measured data in terms of the materials or other properties rather than compositions. In order to reduce the data to the required level of detail, a multi-stage hierarchical grouping in the spectral categories is used in the example embodiment.

The first stage is the SIP mentioned above. The second stage is the "Primary List". The Primary List combines spectral categories from the SIP into smaller numbers of groups that are intended to correspond to recognizable materials and particularly common blends of materials. Since each Primary List material can represent a real material with known physical properties—density, chemical composition, etc.—those properties can be associated with the particle entries through the assignment of each particle entry to one of the Primary List stage categories.

For many analyses, even the Primary List is too detailed, and analysis methods may require further simplification of the material listing down to a few application specific groupings. For this, a third level of grouping is provided referred to as the "Secondary List". The Secondary List groups Primary List categories into a smaller number of Secondary categories. Data can then be analyzed and displayed at this secondary level.

By providing the above-described hierarchical grouping in the example embodiment, the complex detail of the original X-Ray spectra can be reduced to a simple, comprehensible, analysis. This grouping method provides flexibility, allowing grouping to be restructured at any level, without necessarily requiring changes in the hierarchical groupings at any of the other levels.

In order to analyze samples, a series of processing steps must be applied to a selected subset of the particles stored in the database. The example embodiment implements what will be referred to as the "particle stream" model for processing and analyzing the data obtained from the SEM measurements.

The "particle stream" model for processing and analyzing particle data was developed to allow:
  "Real time" calculation and display of processing and analysis results.
  Quick and easy alteration of the processing steps.
  The application of two or more different sets of processing steps to the same population, or to different populations, and comparison of the results from each.

The "particle stream" model considers the data as a stream of individual particles. The particles are drawn from a source and passed through a sequential series of "stages", each of which takes in one or more streams of particles, combines them, then processes and subdivides the combined particles into one or more output streams that can be passed to subsequent processing stages.

Each output stream of a stage can be the input for more than one subsequent stage, resulting in the ability to effectively duplicate a particle stream and apply two different sets of processing to the same particles simultaneously. Each stage can accept input from more than one stream. This allows a stream to be split into disjoint streams at one stage, have different processing stages applied to each stream, and then recombine the split streams into one final stream for analysis. The final stage of a processing stream will gather all of the particles from its input streams and perform a statistical analysis of this particle population and present that to the user in the form of a graph, table or visual image of the particle population.

Each stage in the processing stream is a modular unit, and each unit presents a standard interface to the rest of the data analysis system. Because of this, the stages can be combined in any order and in any sequence, and stages can be added or removed from any point in a sequence of stages. This model allows significant flexibility in the creation and manipulation of processing streams, enabling the requirements described above to be satisfied. The staged structure also provides significant scope for optimizing performance; for example the results can be stored in fast access memory at any stage.

By treating the data as a stream of particle entities, this model allows for powerful, flexible and extensible processing and statistical analysis.

In the example embodiment, Job data objects (described in more detail below with reference to FIG. 3) implement the particle stream processing model. When a Job is activated, it has a single particle stream which draws selected particles from the Datastore, through a customizable series of pre-processor objects, into a staging population in the Job object. This staging population is the "statistically-representative population" that is used in normalization calculations.

The Job object contains multiple Report objects, each of which embodies a single input particle stream, drawing from the Job's staging population and terminating with an analysis and reporting stage. The user utilizing the software can choose to activate any combination of the Reports defined in the Job. When activated, the Report will draw the particles from the Job staging population, through a customizable series of pre-processor objects, into the final Report object. There the particles are accumulated into a report population, and analysis is performed.

Figure 3:
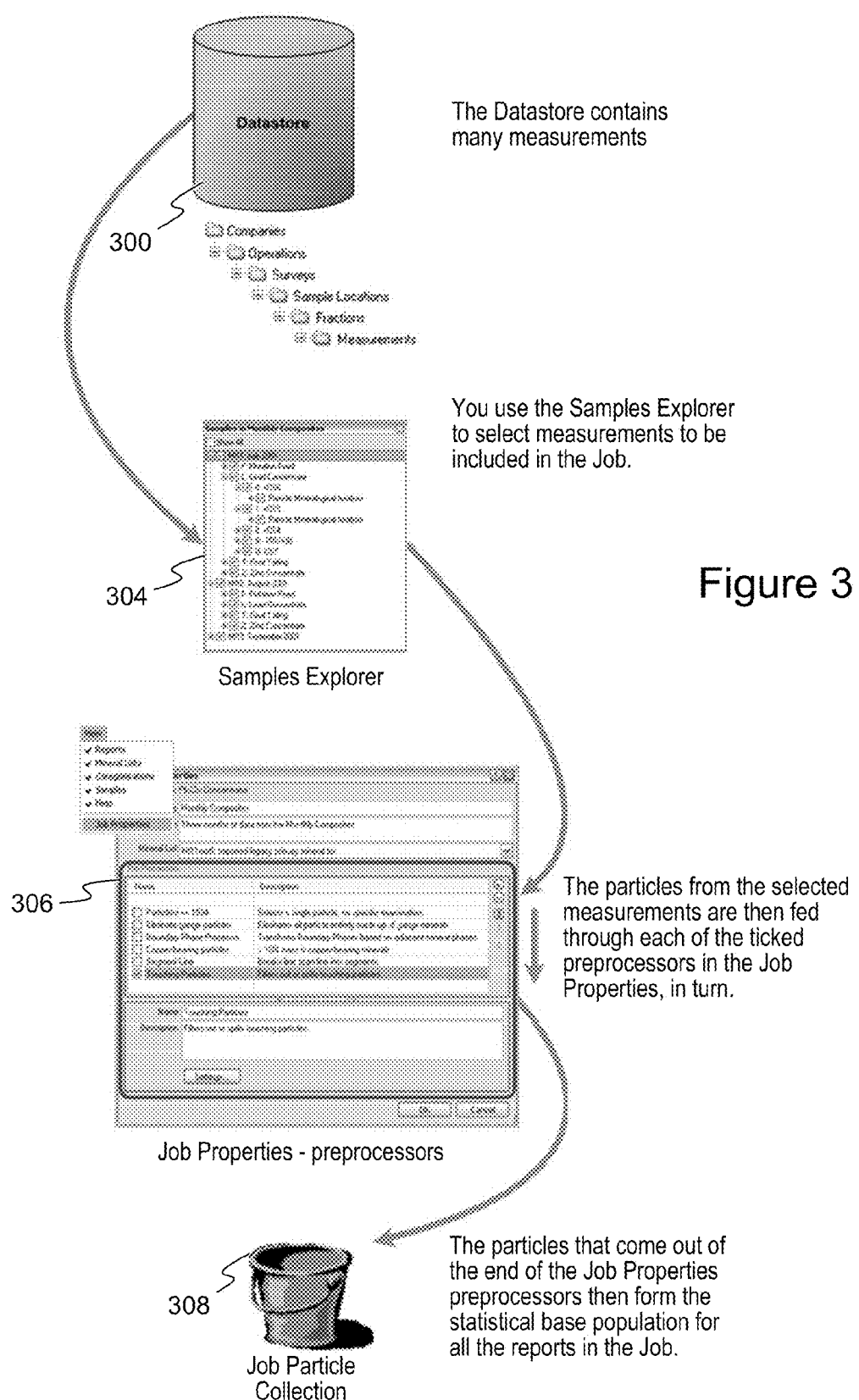
FIG. 3 is a schematic flow chart illustrating a Job Particle Collection process according to an embodiment of the present invention.

FIG. 3 outlines the process of selecting measurements from a Datastore 300 to place into a Job in an example embodiment. The Datastore 300 holds all of the measurements imported, for all of the different Surveys, Operations and Companies a user has defined. The Job belongs to a particular Operation within the Datastore 300, and this automatically restricts it to only accessing measurements that belong to that same Operation.

When the Job is opened, it loads in a collection of particle entities from measurements in the Datastore 300. These particle entities form the statistical basis for the subsequent analyses that are performed. The particle entities that are included in the Job are assumed to be a statistically representative sampling of a fraction of a particular product stream at the time of a survey. Thus if in the Job a particular material makes up 50% of the particle entities in a fraction, then it is extrapolated that 50% of that fraction of the product stream consisted of that material.

The selection of a statistically-representative particle entity population is done in two parts in the example embodiment:
  Select a set of measurements to be included in the Job indicated at numeral 304.
  Pre-processors e.g. 306 are used to filter, edit and modify the particle entities from the selected measurements.

The particle entities that result from this process of selection, filtering and processing then form the Job Statistical Base Population at numeral 308, which is supplied to Reports that are opened in that Job.

Processing and analysis typically consider the different spectral categories found in the particles, and their relative abundances, dispositions and properties. As mentioned above, for ease of interpretation and analysis it is usually desirable to work at a less specific level of categorization than the spectral categories. In this fashion additional physical (or other) properties are introduced to define these less specific categories. This hierarchical grouping is applied to the spectral categories in order to provide powerful and flexible data analysis. The example embodiment utilizes a three-level hierarchy starting with the SIP (Species Identification Profile), then a Primary and Secondary List. In the case of analyzing metallurgical data the hierarchy can be defined as "Primary Mineral List", which combines different spectral categories into a smaller number of groups intended to correspond to known mineral classifications followed by the third level of the hierarchy, the "Secondary Mineral List", which allows primary mineral list groups to be combined into an even smaller number of groups for easier comprehension of the analysis results.

The Primary Mineral List allows additional physical properties, such as density and hardness, to be associated with each group. These properties are important to the calculations performed in the analysis of the data, as they link the measured data to the known physical characteristics of actual minerals. The Secondary Minerals List provides for further customization of the SIP groupings.

A Job also determines the Primary Mineral List to be used when analyzing measurements, and this in turn determines the SIP that must have been used when originally categorizing the spectra taken in the measurements. In the example embodiment one can only analyze measurements that use the same SIP as the Job. Primary List, and hence the SIP, are selected using the Job Properties. In the Job Properties one can select from any of the Primary Mineral Lists available in the Datastore 300. Selecting a Primary Mineral List automatically selects its corresponding SIP.

SIPs and Primary Lists are global in a datastore e.g. 300. Secondary Mineral Lists are specific to a Job. Secondary Lists can be imported into a Job, and/or new Secondary Lists can be created for a Job.

The particle entities that are selected into a Job are very important, not just because these are the measurements that will be available to Reports, but they are used as the statistical basis for many of the calculations. Details of the role of the Statistical Base Population 308 will be described below.

One can specify the total mass-flow that was passing through the product stream sampled. The measurements that are selected into a job are assumed to be a statistically representative sample of this flow in the example embodiment. Therefore, if a particular mineral represents 50% of the selected particle entities, it is assumed from this that 50% of the sampled product stream consisted of that mineral, as mentioned above. When one then asks a question such as "what is the mass of element X in this population", the answer is based on how much element X is in that population, compared to how much is in the Statistical Base Population, adjusted by the mass that was flowing through the product stream at the time of sampling.

Thus selection of an appropriate Statistical Base Population into a Job is important in determining the reasonableness of the resulting calculations. For calculations, the Statistical Base Population is divided up by fraction and by measurement type, so one only needs a good statistical sample for the particular sample fractions and measurement types to be analyzed in a particular Report.

The Statistical Base Population 308 can take up a large amount of computational resources. One of the advantages of the present analysis system is that it enables the selection of only the required measurements needed at the time. When measurements are de-selected, the particle entities and all their calculated properties are released from resources such as computer memory.

A Report in the example embodiment is a plug-in analysis module. It can perform a particular analysis on the sample measurements provided to it. Some Reports are specialized for performing just one very particular analysis. Other Reports are very generalized, and can be tailored to perform a wide variety of functions.

Some typical Reports in the example embodiment include:

| | |
|---|---|
| 3D Chart | A general-purpose, customizable, 3D chart. |
| Modal Analysis | Performs a specialized modal-analysis of sample measurements. |
| Particle View | Allows visual examination of the actual measurement data. |

Reports are created within a Job e.g. 302. Each Report stores configuration properties that are set to control how the report appears, and how it analyzes the data you give it.

The Reports act on the sample measurements selected into the Job. As those selections are changed, the Report output is updated in the example embodiment. When the analysis data required is obtained, the results can be copied from a Report into another application, such as Excel® or Word®. Both chart images and the tabular data they represent can be copied.

Figure 4:
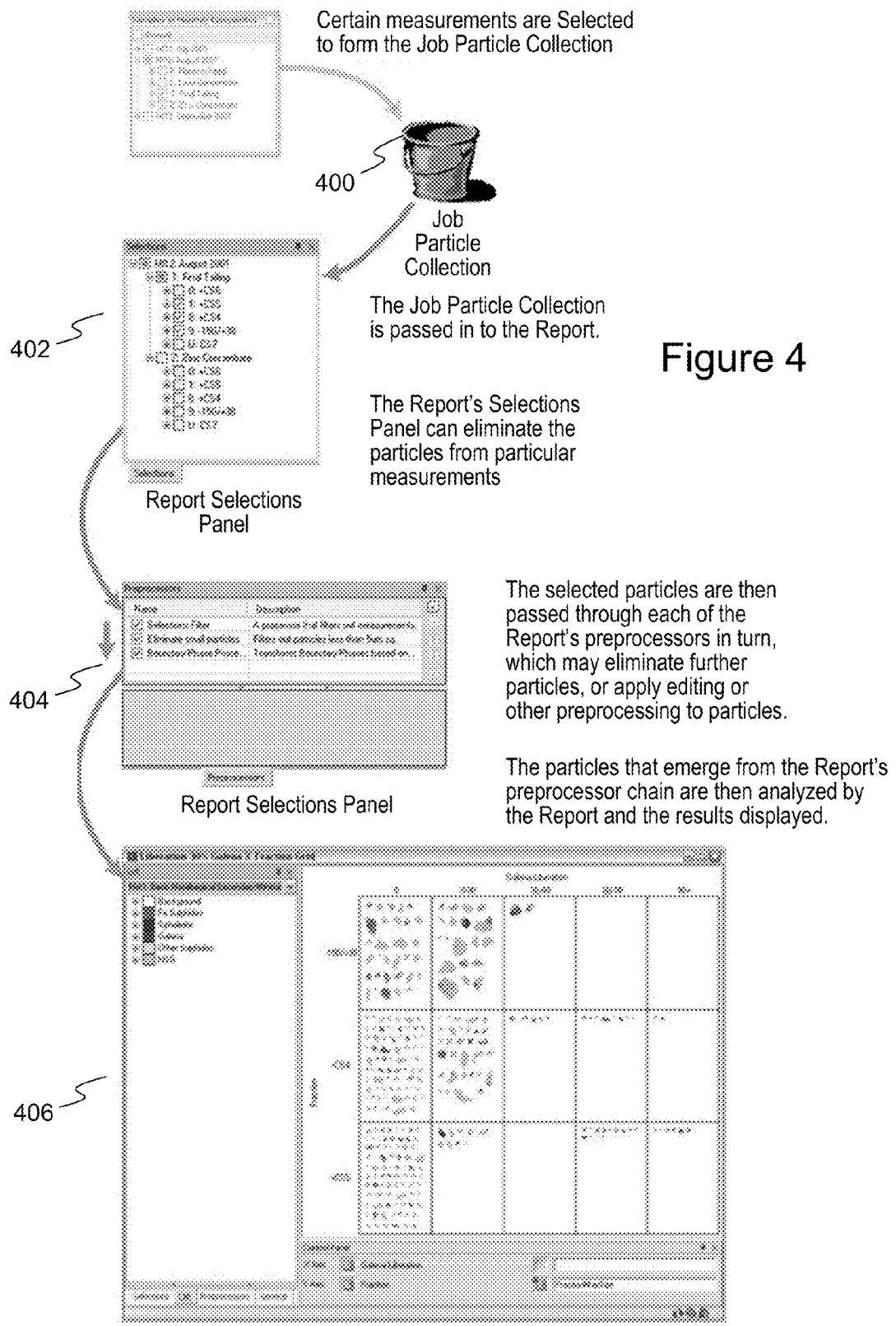
FIG. 4 is a schematic flow chart illustrating a Report process according to an embodiment of the present invention.

FIG. 4 illustrates how data flows into a Report. Reports each belong to a Job, and a Job must be open in order to access the Report. As described above, the act of opening a Job and selecting some measurements creates a Job Particle Population 400 in the Job. Each Report opened draws in the Job Particle Population and analyzes it.

Selection Filtering 402 and preprocessors 404 can be applied to the Report to control what particle entities are analyzed. However, regardless of how one restricts which particle entities are analyzed by a Report, the report still refers back to the Job Particle Population 400 and the general information (such as the sample properties) in the Datastore (not shown) in order to normalize the results for the total mass, volume and surface flow figures.

As illustrated in FIG. 4 one can add filters 400 and preprocessors 402 to a Report, e.g. 406. These can be used to control what particle entities are passed to the Report for analysis, and can apply editing or image processing to the particle entities that are passed through. For example, one can eliminate the barren particle entities (that is, those particles that contain none of a particular material) from a report by adding a Filter preprocessor with an appropriate expression.

Figure 5:
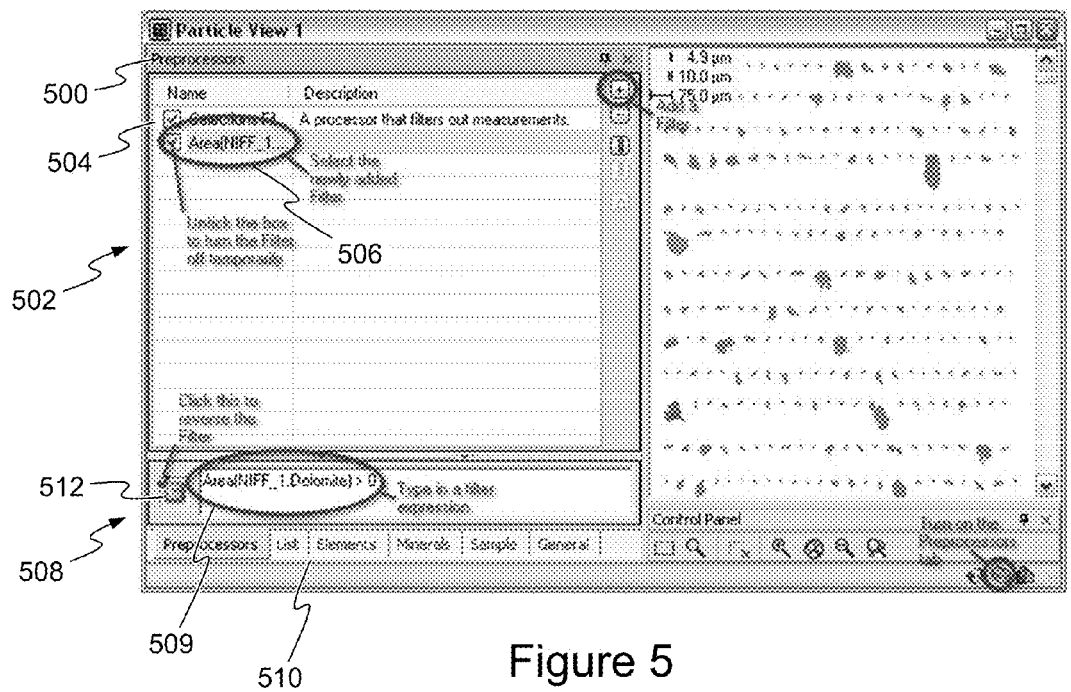
FIG. 5 shows a screen shot of a preprocessor in the process of FIG. 4.

As shown in FIG. 5, to add a preprocessor, the "Preprocessors" panel 500 must be displayed in the report in the Preprocessors panel 502. The "+" button is clicked and the type of processor selected from the processor list 504. Once a new processor e.g. 506 is added it can be edited by clicking, on its entry in the preprocessor list 504. In the panel 508, controls e.g. 512 will appear that allow to adjust the settings of the preprocessor. For example, for a filter, a categorizer slot 509 will appear in the properties area 512. A categorizer can then be entered in the slot 509 that will exclude the appropriate particle entities. For example, to exclude barren particle entities, an expression that tests if the area of a particular material is greater than zero is used. If this expression is 'true', the particle entity will pass through the filter. If the expression is 'false', the particle entity will be rejected. A click on the "tick" 512 on the categorizer slot 509 inverts the filter logic.

A list of Report Templates is displayed whenever one elects to add a new report to a job in the example embodiment. Each report type has specific capabilities. Typical standard templates in the example embodiment are:

|                         |          |
|-------------------------|----------|
| General-purpose         | 2D chart |
| General-purpose         | 3D chart |
| General-purpose         | XY chart |
| Particle Grid           |          |
| Particle View Liberation|          |
| Mineral Association     |          |
| Modal Analysis          |          |
| Operational Statistics  |          |
| Ore Characterization    |          |
| Recovery Analysis       |          |

The Report Templates are "plug-in" components in the example embodiment. This means that they are separate pieces of software to the main application, and can be added or upgraded separately to the main application. This modular system enables to add special custom-written reports to suit particular requirements.

Figure 6:
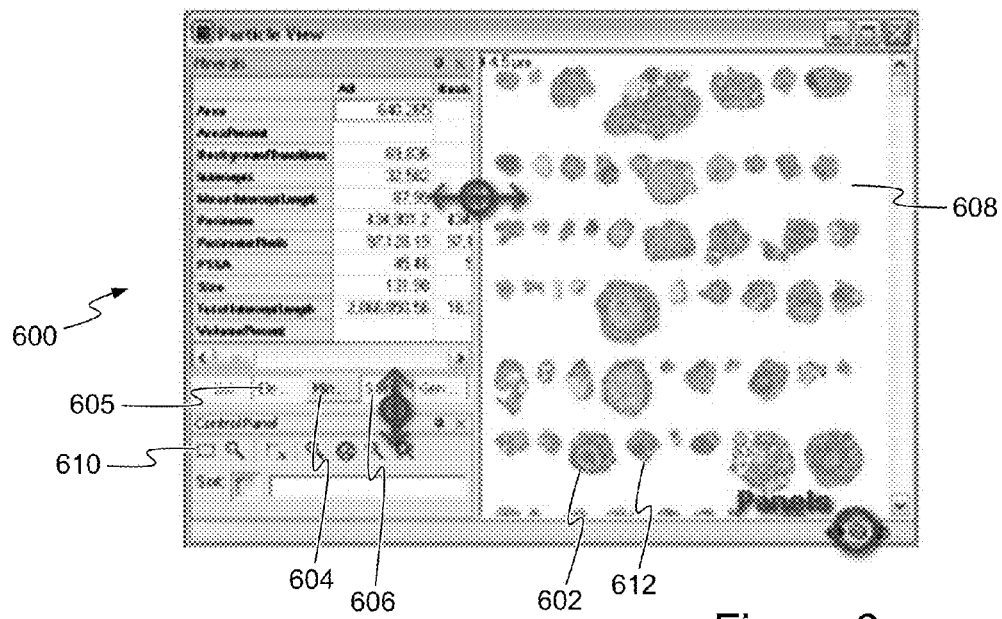
FIG. 6 shows a screen shot of a Report according to an embodiment of the present invention.

FIG. 6 shows an example report 600, entitled "Particle View Report", to examine the individual particle entities e.g. 602 in sample measurements. The Particle View Report 600 allows to view an image of the particle entities e.g. 602 in sample measurements. It also displays material properties, such as mineral and element properties, at numerals 604, 605 respectively, and sample properties (at numeral 606). The Particle View area 608 can be used to mark individual particle entities as "bad", so that they are ignored by all calculations. The controls 610 in the Particle View Report 600 allow to select particle entities within the view area 608, to zoom in and out, and to sort the particle entities e.g. 602 in the display.

In "select" mode, clicking on a particle entity e.g. 602 will select just that particle. Hold down the "Ctrl" key while clicking to toggle particle entities e.g. 602 into or out of the selection. Click and drag to select particle entities e.g. 602, 612 within a box. Material properties such as the Mineral, Element and Sample properties 604, 605, 606 displayed will be those of the selected particle entities. If there are no selected particle entities, the properties will be those of the population as a whole.

Report "Drill-Down" is a special capability of certain reports in the example embodiment. It enables to "drill-down" or investigate further details about subsections of a report viewed. As a general rule, in a report that provides drill-down one can select some part of the displayed data (e.g. a particular column in a chart, or a cell in a Particle Grid), and pop up a new report dealing only with the subset of particle entities in the chosen subsection of the original report.

Figure 7:
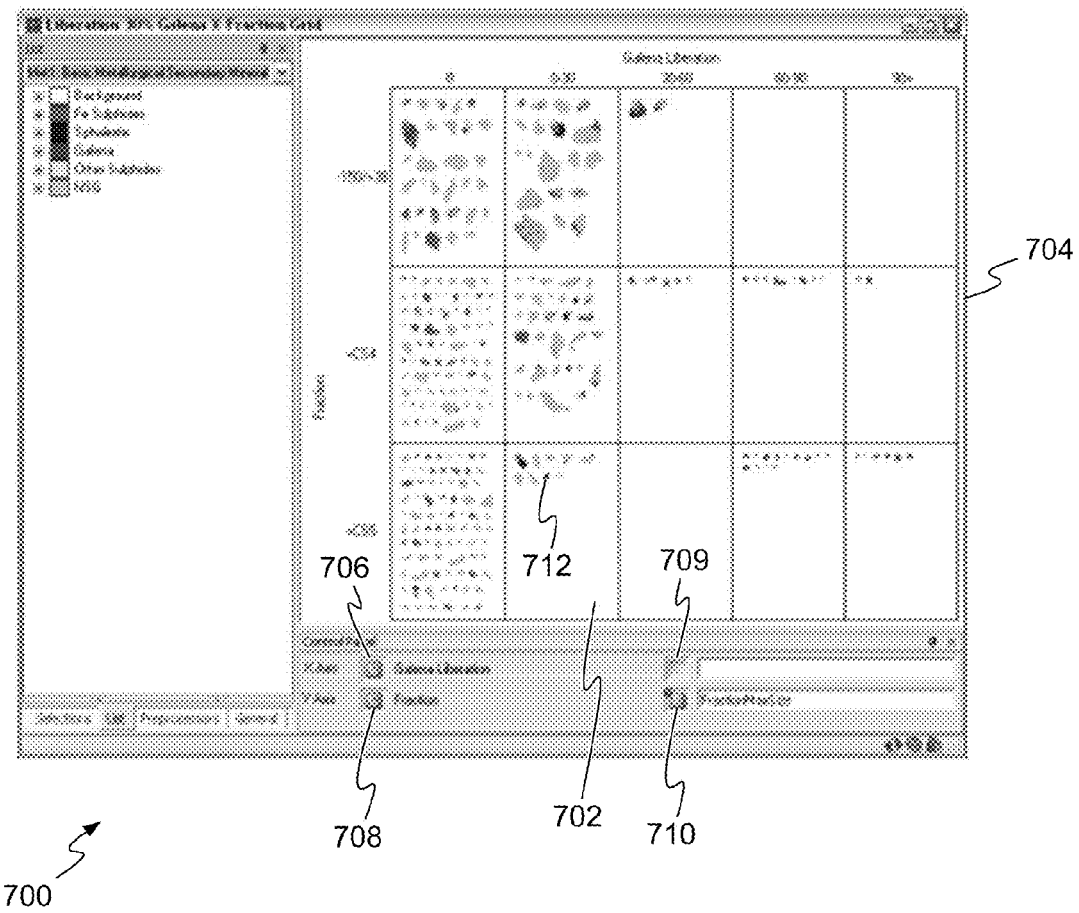
FIG. 7 shows a screen shot of another Report according to an embodiment of the present invention.

For example, in a Particle Grid Report 700 shown in FIG. 7, one can right-click on any cell e.g. 702 in the report 700 and pick "View as . . . " to drill-down. This allows to pop up a new report (not shown) that displays just the particle entities that were in the selected cell of the Grid area 704. If a change is made in the original Report 700—e.g. change the selected samples, or click a different cell in the Grid area 704—the change will be reflected in the drill-down report.

The "drill-down" capability is made possible by the modular nature of the "particle stream" processing model underlying the implementation, and demonstrates some of the power and flexibility that model allows. Any sub-population of particles within a report can be made available as an output particle stream to further stages of processing, analysis and display.

In "drill-down" one can either select a new report (of any type) to display, or select from a pre-configured Drill-Down Template report. A Drill-Down Template is any report whose Usage property has been set to "Drill-Down Template". The reports that pop up for selection in a drill-down are transient—they are not saved in the Job, and will disappear when the original report from which they were popped up is closed. However, one can save a template of the pop-up report. This will enable an identically-configured report to pop up next time.

The Particle Grid Report 700 shown in FIG. 7 is a customizable report that uses two Categorizers 706, 708 and two Calculated Values e.g. 709, 710 to divide the measurements into a grid 704 of particle entity populations, e.g. in cell 702. It then displays a thumbnail image of the particle entities e.g. 712 in each grid cell e.g. 702. The two Categorizers 706, 708 determine how the particle entities are divided in the x and y axes. The two Calculated Values 709, 710 determine how the categories on each axis are sorted.

The expressions used in the calculated Values 709, 710 Categorizers 706, 708 allow for user definable constraints to be set at a more fundamental level than the preprocessors function described above. The expression system in the example embodiment has access to data at all levels of schema structure for all particle entities. Examples of user definable calculations based on the properties of the particle entities fall into categories such as:

Calculated properties such as area, mass and other properties related to composition or texture.

Sample schema properties such as how the mass was flowing through a particular location when the sample was taken.

The power and flexibility of the example embodiment is, to a large part, achieved through the use of customizable categorizations, calculations and filtering. The foundation of all of these functionalities is a mathematical expression language in the example embodiment. This language allows the writing of mathematical expressions that perform calculations based on the properties of minerals, measured particle entities, and collections of measured particle entities. This functionality is facilitated by recognizing the particle entity as the fundamental sample unit.

Expressions are the building-blocks for reports and are found primarily in Particle Categorizers and Calculated Values (706, 708, 709, 710 see e.g. in FIG. 7). They define the categories displayed in charts and tables and the values calculated in those charts and tables. They are also used to define sorting and to create filters to select subsets of particles from the particle stream, as described above with reference to FIGS. 3 and 4.

An expression is a sequence of operators and operands, and is applied to a particular context. When expressions are evaluated, it is done in a specific 'context'. The context is simply where and how the expression is being used. For example, an expression being used to sort categories on the axis of a chart is one context. A expression being used to filter the particle entities going into a report is another context. The context determines:

The mineral lists available to the expression.

The 'target' of the expression—whether it is calculated for each particle entity individually or a collection of particle entities as a whole (a 'population').

The appropriate return value of the expression—whether the expression should calculate a number, a string or a Boolean value.

Available Mineral Lists

All expressions are evaluated within the over-all context of the currently open Job, and the mineral lists available are those available within the job. Thus there will always be one SIP mineral list and one Primary mineral list. There may also be one or more Secondary Mineral Lists.

Expression Targets

The target of an expression is determined by where it is used. Expressions used in Particle Categorizers are always calculated for individual particle entities, so their target is a particle. Expressions used in Calculated Values are always calculated for a population, so their target is the population.

Understanding the expression's target is important, because a property in an expression refers to a property of the target. Thus if an expression refers to "Area", then when used in a Particle Categorizer it refers to the Area of an individual particle. When used in a Calculated Value, it instead refers to the sum-total area of all the particle entities in the population. This ability to determine properties for either a single particle, or the equivalent property for an entire collection of particles as a whole, is important to the implementation in the example embodiment. Each property that can be calculated includes, if possible, logic to support both cases. In cases where the calculation cannot be performed, an error message is produced.

In the example embodiment, all available properties can be calculated for both the particle and collection cases, except for the "Shape Factor" property, which can only be calculated for an individual particle. One simple case might be the calculation of what proportion of the cross-sectional area of a collection of particles occurs in the form of the mineral Pyrite. To do this, the software will first determine which spectral categories are to be considered "Pyrite". Assuming "Pyrite" is a secondary mineral list grouping, the software will determine what primary mineral list groupings are included in "Pyrite", and then what SIP spectral categories are included in those primary mineral list groupings. This will result in a (potentially large) list of spectral categories that are considered to be "Pyrite". The software will then iterate through all of the particles in the collection of particles, and for each particle count the total number of measurement spots that were assigned a spectral category that is considered to be "Pyrite". This gives a measure of the cross-sectional area of "Pyrite" in the particle. In the case of area, the total area of "Pyrite" for a collection of particles can be obtained by simply summing the areas for the individual particles.

A more complex example is the calculation of mass—for example, the mass of "Pyrite" represented by a particle collection. This calculation proceeds in the same manner as the "Area" example above, but the area totals for each particle have to be summed at the Primary Mineral List grouping level. At this point, the area totals for each primary mineral list grouping are multiplied by the Density property assigned to that primary mineral list grouping, to give a dimensionless "mass unit" value. The mass unit values can then be summed to give a total mass unit value for "Pyrite" in that particle.

The total mass is calculated by summing the Pyrite mass for each particle, but to do that, each particle's pyrite mass units value has to be converted into a single uniform frame of reference—that of absolute mass. This process is referred to as "normalization", and requires the statistically-representative population mentioned earlier.

To normalize the mass units, it is necessary to first calculate the total corresponding mass units present in the statistically representative population. Having done this, one only needs to know what absolute mass is represented by the statistically representative population. This is done by subdividing the statistically representative population on the basis of the sample and fraction objects of the hierarchical data organization in the example embodiment, as described above. For each sample object, the general information includes the total absolute mass of which that sample object is a statistical representative. For each fraction object, the general information includes the proportion of the sample object mass that occurs in that fraction object.

Because each particle retains all of its contextual information through the inter-relation, inter alia, between particle objects, sample objects and fraction objects, it is known which sample and fraction object each particle belongs to, and so the total absolute mass, and the total mass units, for the statistically representative population can be determined. The mass units for each particle can be converted to absolute mass, and accumulated with the absolute masses of other particles. It is noted that this is regardless of the sample or fraction from which the respective particles originated. This enables "normalized" analysis for combinations and comparisons of particles from different parts of a physical sample and/or from different physical samples.

In the course of analyzing particles, some situations require the method to process particles that are touching or almost touching. When samples are measured, it is important that each physical particle be recognized as such. Because of the physical limitations of the sample preparation process, it is not possible to guarantee that all particles in the sample are physically separated. The situation may arise where particles will be in contact, or appear to be so at the resolution of the measured data. In the case where the proportion of "touching particles" is significant then treating a group of two or more closely spaced particles as a single particle may lead to incorrect data analysis and interpretation.

The example embodiment includes a method for detecting when a particle measurement may actually be several separate particles, and a method for splitting the data for such a particle into separate "particles" for subsequent analysis. Existing algorithms for this type of process typically use image analysis of "grey scale" images, and use pixel-oriented processing algorithms such as "erode", "dilate" and "watershed algorithms". The example embodiment uses a different approach, based on the measured material information and the perimeter profile of the particle. The method examines the perimeter profile of the particle, looking for "cusps" and indentations as clues to touching particles.

The method then uses the measured material data to calculate possible "split paths" representing where the touching particles touch. In doing this, it uses heuristic logic to calculate a path that preferentially follows boundaries between materials. The method relies on the knowledge of materials and compositions (as indicated by the spectral categories) that are likely to be detected at the boundary between two touching particles.

In order to determine if a particular particle is in fact two or more touching particles, a recursive analysis is performed in the example embodiment as follows:

Firstly the bounding dimensions of the particle are considered based on the measurement spots assigned to the particle, and particles that are deemed too small in either dimension are rejected as "non-touching".

Next an approximate measure of the "roundness" of the particle is determined, by considering the ratio of the square of its perimeter to its area. Particles that fall below a certain limit are rejected as "non-touching".

The perimeter profile of the particle is then analyzed, to detect "cusps"—places where the perimeter dips towards the opposite side. This is done using a two-stage process: first selecting a set of arbitrary "probe points" around the perimeter and looking for cusps that dip towards those points, and then repeating that process using the identified cusp points as the "probe points".

The cusp-detection process is then repeated a third time, using the cusp points obtained from the preceding stage. This produces a list of "mutually interested" cusp pairs—pairs of cusp that appear to dip towards each other.

This list of cusp pairs is then culled, based on some simple geometric analysis of the potential splits that they would produce. Splits that are considered "too long" or fragments that would be "too large" or "too small" according to a set of adjustable parameters are rejected.

Any cusp pairs that survive the simple geometric cull are then analyzed for "relative velocity". This is a heuristic analysis of the overall shape of the cusp, assessing how steep and sharp it is. This is done by treating the "target cusp" as a gravitational attractor, and simulating the motion of a body moving around the perimeter to the cusp being analyzed. The simulated velocity of the body when it reaches the cusp is the "relative velocity" of the cusp. The relative velocity is assessed both clockwise and counter-clockwise. Certain damping and attenuation factors are applied in the simulation to emphasize the localized effects around the cusp itself.

If the total relative velocity of a cusp pair is insufficient, it is culled from the list.

If there are any cusp pairs remaining, the particle is considered to in fact be two or more touching particles.

If we then wish to split the particle, we perform a detailed split-analysis. This consists of calculating an optimal-path split through the particle for each remaining cusp pair. The "cost" of the path is assessed based on the spectral categories or groupings of the points the split-path passes between. The path with the lowest "cost" is then selected, and the particle split on that basis.

The same analysis process is then re-applied to each particle resulting from the split.

This analysis determines whether the fragment should be represented as part of the particle or a separate particle.

When a QEMSCAN system measures a sample, the resulting data is a map of compositions, which is interpreted to determine the materials present in the sample. Because the electron beam used to scan the sample excites a volume, and the volume usually contains more than one material, the compositions measured represent varying blends of materials present. This process often produces undesirable artefacts at the boundaries between different materials.

The example embodiment includes a method to eliminate such boundary artefacts. This enables accurate analysis of the data. The method uses a rules-based pattern recognition system to first identify then eliminate the boundary-phase artefacts. The rules utilized by the system are expressed in terms of material categories at one of the levels of the multi-level hierarchical grouping of measured data. In the example embodiment, the rules are applied at the Primary List level.

The rules-based system uses a three-point filter, which is applied across the rows and/or down the columns of the spectral category data within each fundamental sample unit. The filter examines each cluster of three data points in turn, and applies its pattern-recognition rules. The rules define allowed transformations of the "middle" data point in each cluster of three, based on its spectral category and the spectral category of the two adjacent data points. In general, if the pattern of spectral categories matches one of the rules, the middle data point will be changed to be the same category as either the preceding or the following data point. The rules can be defined by the software operator, based on their knowledge of the materials being analyzed and the artefacts typically encountered in their measurements.

Figure 8:
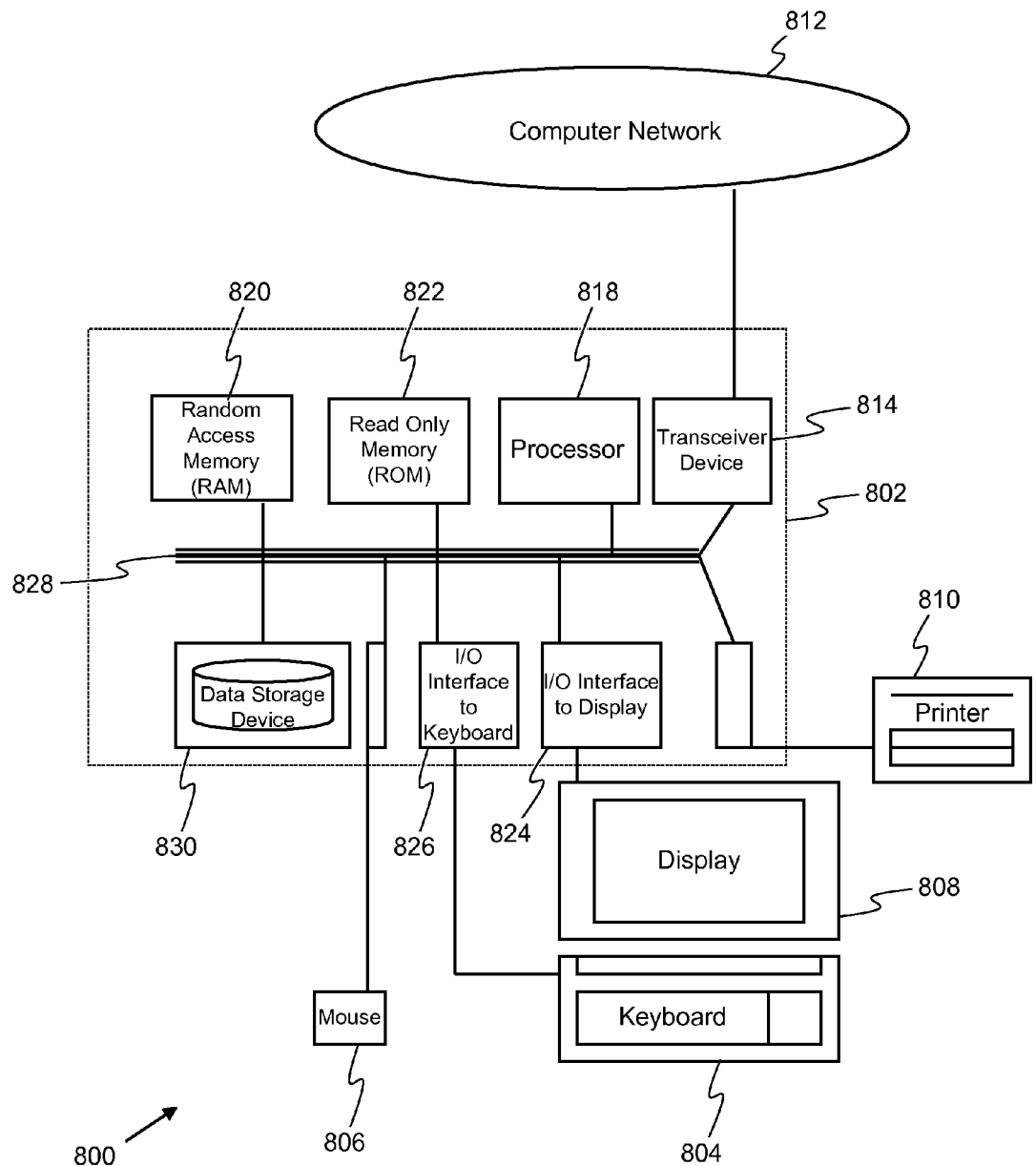
FIG. 8 shows a schematic drawing of a computer system for implementing a spectroscopic data analysis system according to an embodiment of the present invention.

The method and system of the example embodiment can be implemented on a computer system 800, schematically shown in FIG. 8. It may be implemented as software, such as a computer program being executed within the computer system 800, and instructing the computer system 800 to conduct the method of the example embodiment.

The computer system 800 comprises a computer module 802, input modules such as a keyboard 804 and mouse 806 and a plurality of output devices such as a display 808, and printer 810.

The computer module 802 is connected to a computer network 812 via a suitable transceiver device 814, to enable access to e.g. the Internet or other network systems such as Local Area Network (LAN) or Wide Area Network (WAN).

The computer module 802 in the example includes a processor 818, a Random Access Memory (RAM) 820 and a Read Only Memory (ROM) 822. The computer module 802 also includes a number of Input/Output (I/O) interfaces, for example I/O interface 824 to the display 808, and I/O interface 826 to the keyboard 804. The components of the computer module 802 typically communicate via an interconnected bus 828 and in a manner known to the person skilled in the relevant art.

The application program is typically supplied to the user of the computer system 800 encoded on a data storage medium such as a CD-ROM or floppy disk and read utilizing a corresponding data storage medium drive of a data storage device 830. The application program is read and controlled in its execution by the processor 818. Intermediate storage of program data may be accomplished using RAM 820.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

We claim as follows:

1. A method of analysing spectroscopic data the method comprising:

directing an electron beam onto a sample;

collecting spatially resolved measurement x-ray spectroscopic data of a sample for a series of measurements spots, the x-rays generated by the impact of the electron beam at each measurement spot;

assigning the measurement spots into a predefined set of spectral categories, based on characteristics of the spectroscopic data of the respective measurement spots;

identifying groupings of the measurement spots based on their respective spectral categories and their spatial relationships;

assigning each grouping of measurement spots to a fundamental sample unit data object; and utilizing a hierarchical structure of general information data objects that embody the hierarchical relationships of the general information assigned to the fundamental sample unit data objects, with relationships defined as being either "up" the hierarchy, that is away from the fundamental sample unit data objects, or "down" the hierarchy, that is towards the fundamental sample unit data object, and wherein the general information assigned to a fundamental sample unit data object is stored in the general information data object in the hierarchical structure that represents the manner in which said general information data is shared by the fundamental sample unit data objects.

2. The method as claimed in claim 1, wherein data items obtainable from each general information data object in the hierarchical structure comprise all of the data items stored in said general information data object, plus all data items obtainable from general information data objects further "up" the hierarchical structure.

3. The method as claimed in claim 1, wherein the hierarchical structure and choice of storage locations within the hierarchical structure follow a predefined pattern.

4. The method as claimed in claim 1, wherein the hierarchical structure and choice of storage locations within the hierarchical structure are determined and changed dynamically as-needed.

5. The method as claimed in claim 1, further comprising assigning one or more properties to each spectral category.

6. The method as claimed in claim 1, further comprising assigning general information, including measurement information and/or sample information, to each fundamental sample unit data object.

7. The method as claimed in claim 6, further comprising calculating one or more derived properties for each fundamental sample unit data object based on one or more of a group comprising the measurement spots assigned to the fundamental sample unit data object, the one or more properties assigned to the spectral categories of the measurement spots, the general information assigned to the fundamental sample unit data object, and the spatial relationships of the measurement spots.

8. The method as claimed in claim 7, wherein the derived properties comprise one or more of a group comprising mass, area, perimeter, volume, size and density.

9. The method as claimed in claim 1, wherein the predefined set of spectral categories comprises a hierarchical grouping of categories.

10. A method of analysing spectroscopic data the method comprising:
    directing an electron beam onto a sample;
    collecting spatially resolved measurement x-ray spectroscopic data of a sample for a series of measurements spots, the x-rays generated by the impact of the electron beam at each measurement spot;
    assigning the measurement spots into a predefined set of spectral categories, based on characteristics of the spectroscopic data of the respective measurement spots;
    identifying groupings of the measurement spots based on their respective spectral categories and their spatial relationships;
    assigning each grouping of measurement spots to a fundamental sample unit data object;
    formulating an analysis query; and
    defining the analysis query as a sequential series of processing stages, each processing stage having one or more inputs and one or more outputs;
    wherein, during execution of the analysis query, one or more of the fundamental sample unit data objects are sequentially provided to each processing stage input as input streams, and processed and output as respective output streams of fundamental sample unit data objects at each processing stage output; and
    wherein the output stream or streams from one processing stage are the input streams for the next processing stage in the sequential series of processing stages.

11. The method as claimed in claim 10, wherein the processing at each processing stage comprises:
    passing a received fundamental sample unit data object as-is to one or more processing stage outputs, or
    creating one or more new fundamental sample unit data objects based on the received fundamental sample unit data object, wherein the new fundamental sample unit data objects inherit the general information assigned to the received fundamental sample unit data object and retain a reference back to the received fundamental sample unit data object, and passing each new fundamental sample unit data objects to one or more processing stage outputs.

12. The method as claimed in claim 11, wherein one or more logical expressions are utilised for assigning the received or the new fundamental sample unit data objects to one or more of the processing stage outputs.

13. The method as claimed in claim 11, wherein the new fundamental sample unit data object is created to separate respective groupings of measurement spots which were initially assigned to one fundamental sample unit data object.

14. The method as claimed in claim 11, wherein one of the processing stages produces a statistically representative population of fundamental sample unit data objects as the output stream for normalisation processing in subsequent processing stages.

15. The method as claimed in claim 14, wherein the statistically representative population of fundamental sample unit data objects comprises fundamental sample unit data objects from different samples.

16. The method as claimed in claim 10, further comprising assigning one or more properties to each spectral category.

17. The method as claimed in claim 10, further comprising assigning general information, including measurement information and/or sample information, to each fundamental sample unit data object.

18. The method as claimed in claim 10, wherein the predefined set of spectral categories comprises a hierarchical grouping of categories.

* * * * *